(12) United States Patent
Bhatnagar et al.

(10) Patent No.: US 9,222,864 B2
(45) Date of Patent: Dec. 29, 2015

(54) APPARATUS AND METHOD TO MEASURE BACK FACE SIGNATURE OF ARMOR

(75) Inventors: Ashok Bhatnagar, Richmond, VA (US); Henry Gerard Ardiff, Chesterfield, VA (US); David A. Hurst, Richmond, VA (US); Thomas Yiu-Tai Tam, Chesterfield, VA (US); Tyler Bartelt, Midlothian, VA (US); Brian Duane Arvidson, Chester, VA (US)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 519 days.

(21) Appl. No.: 13/594,757

(22) Filed: Aug. 24, 2012

(65) Prior Publication Data

US 2013/0055790 A1 Mar. 7, 2013

Related U.S. Application Data

(60) Provisional application No. 61/531,233, filed on Sep. 6, 2011.

(51) Int. Cl.
| | |
|---|---|
| *G01N 3/30* | (2006.01) |
| *G01N 3/313* | (2006.01) |
| *F41H 5/00* | (2006.01) |
| *F41H 5/02* | (2006.01) |

(52) U.S. Cl.
CPC .............. *G01N 3/313* (2013.01); *G01N 3/30* (2013.01); *F41H 5/00* (2013.01); *F41H 5/02* (2013.01)

(58) Field of Classification Search
CPC ..................................................... G01N 3/313
USPC ....................................................... 73/12.11
See application file for complete search history.

(56) References Cited

U.S. PATENT DOCUMENTS

| | | | |
|---|---|---|---|
| 3,771,418 A | * | 11/1973 | Gulbierz et al. ............. 89/36.02 |
| 4,161,874 A | | 7/1979 | Specker et al. |
| 4,691,556 A | | 9/1987 | Mellander et al. |
| 4,952,361 A | | 8/1990 | Cree |

(Continued)

FOREIGN PATENT DOCUMENTS

| | | |
|---|---|---|
| CN | 101603797 | 12/2009 |
| EP | 412452 A2 * | 2/1991 |

(Continued)

OTHER PUBLICATIONS

U.S. Department of Justice Office of Justice Programs National Institute of Justice, NIJ Standards Ballistic Resistance of Body Armor NIJ Standard-0101.06, Jul. 2008.*

(Continued)

*Primary Examiner* — Laura Martin
*Assistant Examiner* — Herbert K Roberts
(74) *Attorney, Agent, or Firm* — Roberts & Roberts, LLP; Richard S. Roberts, Jr.

(57) ABSTRACT

An apparatus and method are provided for evaluating the backface signature of flat panel ballistic resistant composites with accuracy, repeatability and improved correlation to the expected backface signature of shaped ballistic resistant composites in actual field use. The apparatus separates the composite from a clay backing material with a suitable spacer so that the bulk of the backface deformation is inside an air gap space with minimal clay disturbance, thereby eliminating conventional testing error and producing an accurate test result.

20 Claims, 5 Drawing Sheets

(56) References Cited

U.S. PATENT DOCUMENTS

| | | | |
|---|---|---|---|
| 5,001,008 A | 3/1991 | Tokita et al. | |
| 5,075,904 A | 12/1991 | Shirasaki et al. | |
| 5,139,873 A | 8/1992 | Rebouillat | |
| 5,178,802 A | 1/1993 | Cree et al. | |
| 5,534,343 A * | 7/1996 | Landi et al. | 428/313.5 |
| 5,545,455 A | 8/1996 | Prevorsek et al. | |
| 5,569,528 A | 10/1996 | Van der Loo et al. | |
| 5,573,850 A | 11/1996 | Cunningham et al. | |
| 5,591,933 A | 1/1997 | Li et al. | |
| 5,601,775 A | 2/1997 | Cunningham et al. | |
| 5,677,029 A * | 10/1997 | Prevorsek et al. | 428/113 |
| 6,326,427 B1 | 12/2001 | Birnbrich et al. | |
| 6,630,231 B2 | 10/2003 | Perez et al. | |
| 6,691,585 B2 | 2/2004 | Ahn | |
| 7,163,205 B1 * | 1/2007 | Kecskes et al. | 273/410 |
| 7,204,165 B1 | 4/2007 | Plaga et al. | |
| 7,718,245 B2 | 5/2010 | Bhatnagar et al. | |
| 7,762,175 B1 * | 7/2010 | Bhatnagar et al. | 89/36.02 |
| 7,856,340 B2 * | 12/2010 | Kaneko et al. | 702/179 |
| 7,964,518 B1 | 6/2011 | Bhatnagar et al. | |
| 2001/0031594 A1 | 10/2001 | Perez et al. | |
| 2003/0199215 A1 | 10/2003 | Bhatnagar et al. | |
| 2004/0118271 A1 * | 6/2004 | Puckett et al. | 89/36.02 |
| 2007/0016251 A1 | 1/2007 | Roby | |
| 2007/0117483 A1 | 5/2007 | Bhatnagar et al. | |
| 2008/0139071 A1 | 6/2008 | Bhatnagar et al. | |
| 2008/0289438 A1 | 11/2008 | Bertocci | |
| 2009/0115099 A1 | 5/2009 | Goossens et al. | |
| 2009/0197969 A1 | 8/2009 | Poulsen et al. | |
| 2009/0282596 A1 | 11/2009 | Carbajal et al. | |
| 2009/0305038 A1 | 12/2009 | Duran et al. | |
| 2010/0048076 A1 | 2/2010 | Creyghton et al. | |
| 2010/0083733 A1 * | 4/2010 | Russell et al. | 73/12.01 |
| 2010/0186134 A1 * | 7/2010 | Hunter et al. | 2/2.5 |
| 2010/0196671 A1 | 8/2010 | Sorensen et al. | |
| 2010/0307223 A1 | 12/2010 | Jeftic-Stojanovski et al. | |
| 2011/0041679 A1 | 2/2011 | Pollock et al. | |
| 2011/0113951 A1 * | 5/2011 | Daley et al. | 89/36.02 |
| 2013/0055790 A1 * | 3/2013 | Bhatnagar et al. | 73/12.11 |
| 2013/0059112 A1 | 3/2013 | Tam et al. | |
| 2013/0059494 A1 | 3/2013 | Tam et al. | |
| 2013/0059496 A1 | 3/2013 | Ardiff et al. | |

FOREIGN PATENT DOCUMENTS

| | | |
|---|---|---|
| EP | 572965 A1 * | 12/1993 |
| JP | 1986-241330 | 10/1986 |
| JP | 61241330 | 10/1986 |
| JP | 62169827 | 7/1987 |
| JP | 62184111 | 8/1987 |
| JP | 2269828 | 11/1990 |
| JP | 05209370 | 8/1993 |
| JP | 06212504 | 8/1994 |
| JP | 6-346372 | 12/1994 |
| JP | 7-138877 | 5/1995 |
| JP | 07135087 | 5/1995 |
| JP | 08049998 | 2/1996 |
| JP | 2001-262469 | 9/2001 |
| KR | 10-0567442 | 4/2006 |
| KR | 10-0601829 | 7/2006 |
| KR | 2011037383 A * | 4/2011 |
| KR | 20110037383 | 4/2011 |
| SE | 200400725 | 9/2005 |
| WO | WO 9423263 A1 * | 10/1994 |
| WO | WO 9602691 A1 * | 2/1996 |
| WO | 2006040754 | 4/2006 |
| WO | 2007057595 | 5/2007 |
| WO | 2007148365 | 12/2007 |
| WO | 2008133735 | 11/2008 |
| WO | 2010123593 | 10/2010 |
| WO | 2011015620 | 2/2011 |
| WO | 2011043501 | 4/2011 |

OTHER PUBLICATIONS

Department of Defense Army Research Laboratory, Weapons & Materials Research Directorate, Department of Defense Test Method Standard MIL-STD-662F, Dec. 18, 1997.*

Yang, Zingzhou (James), and Jichang Dai, "Simulation-Based Assessment of Rear Effect to Ballistic Helmet Impact." Computer-Aided Design & Applications, 7(1), 2010, pp. 59-73.

Aare, Magnus, and Svein Kleiven, "Evaluation of Head Response to Ballistic Helmet Impacts Using the Finite Element Method." International Journal of Impact Engineering 34 (2007), pp. 596-608.

"Ballistic Load Sensing Headform", Biokinetics & Associates, Ltd. Brochure.

"Body Armor Follow-Up Testing Component Launched." TechBeat, Fall 2010, National Law Enforcement and Corrections Technology Center, National Institute of Justice.

"Supplement 1: Status Report to the Attorney General on Body Armor Safety Initiative Testing and Activities." National Institute of Justice, Dec. 27, 2004.

"Bullet Resistant Helmet" Test Procedure, H.P. White Laboratory, Inc., Oct. 1995.

"NIJ Standard for Ballistic Helmets." Technology Assessment Program, Dec. 1981.

"Ballistic Resistance of Personal Body Armor, NIJ Standard-0101. 04," National Institute of Justice, Law Enforcement and Corrections Standards and Testing Program, Sep. 2000.

"Head Strong: ARL Team Determined to Find New Solutions for Improved Soldier Helmet Systems," Mar. 1, 2011.

"Test and Evaluation Report on Marine Corps Combat Helmets," Apr. 8, 2001.

Unpublished U.S. Appl. No. 13/594,735, filed Aug. 24, 2012.
Unpublished U.S. Appl. No. 13/594,747, filed Aug. 24, 2012.
Unpublished U.S. Appl. No. 13/594,763, filed Aug. 24, 2012.

Moon, S.I. et al., "The Effect of the Oxygen-Plasma Treatment of UHMWPE Fiber on the Transverse Properties of UHMWPE-Fiber/Vinylester Composites." Composites Science and Technology, vol. 59 (Mar. 1999), pp. 487-493, Seoul, South Korea.

* cited by examiner

APPARATUS AND METHOD TO MEASURE BACK FACE SIGNATURE OF ARMOR

CROSS-REFERENCE TO RELATED APPLICATION

This application claims the benefit of U.S. Provisional Application Ser. No. 61/531,233, filed on Sep. 6, 2011, the disclosure of which is incorporated by reference herein in its entirety.

BACKGROUND OF THE INVENTION

1. Field of the Invention

This invention relates to an apparatus and method for evaluating the backface signature of flat panel ballistic resistant composites in correlation to the expected backface signature of shaped ballistic resistant composites in actual field use.

2. Description of the Related Art

In the field of body armor, there are an increasing number of suitable materials assembled or converted into ballistic resistant articles. These ballistic resistant articles include soft body armor for protection of the torso and extremities against certain threats, molded rigid plates which protect the torso against higher level threats, and molded rigid helmets which protect the head against a variety of threats. It is known that in addition to stopping bullets or projectiles, it is desirable for the armor to limit or minimize its own deflection back into the wearer during a ballistic event. This deflection is known in the industry as trauma, blunt-force trauma, backface deformation or backface signature (BFS). In the area of soft body armor, the article typically rests directly on or very close to the body of the user, and thus a reasonable approximation or prediction of BFS that may be expected during a ballistic event in field use may be measured by laying the article directly on a flat block of an deformable, oil-based clay, firing a projectile into the article, and then measuring the depth or volume of the resulting hole in the clay block. In the area of molded rigid armor, the same protocol may be used to obtain a reasonable approximation or prediction of BFS that may be expected during a ballistic event in field use for molded armor that rests directly on or very close to the body of the user.

However, such an approximation or prediction of BFS for rigid helmet armor is much more difficult because by rule the armor component of the helmet does not lie directly on the head of the user. Conventionally, helmets are designed with a variable off-set or stand-off distance that will vary due to the size and shape of the helmet interior relative to the size and shape of the head of the user. The minimum distance will generally be set or defined by a series of pads attached to the interior of the helmet, and an interior harness or retention system may increase this distance even more. Methods to measure the BFS of a prototype or finished helmet have been developed to approximate BFS of shaped helmets in a real end-use environment. One accepted technique begins with a metallic head form that has large sections removed. These sections are filled with clay and the clay is smoothed to a reasonable approximation of the contour of the human head. A prototype helmet is then placed on this head form and tested. Measurement of the depth and volume of the holes in the clay should give a reasonable approximation of the BFS that will be expected in field use when the helmet encounters a projectile.

As new materials are developed and evaluated, it is not always desirable, cost effective or prudent to fabricate a prototype helmet from each material intended for BFS testing. It is much simpler and thus preferred to conduct initial screening on molded flat panels, which are easier to produce, easier to work with during testing, and result in a hole or deformation that is easier to measure and evaluate. Unfortunately, data has shown that measurement of BFS using molded flat panels placed directly on clay does not correlate well with the actual in field helmet performance of materials. The present invention provides a solution to this problem in the art, providing an apparatus and method for testing molded flat panel composites for accurately determining the expected backface signature of ballistic resistant composites in actual field use, and avoiding the current need to produce helmet prototypes.

SUMMARY OF THE INVENTION

The invention provides an apparatus for evaluating the backface signature of a fibrous material, the apparatus comprising:
a) a deformable backing medium having a front surface;
b) a spacer defining a space adjacent to said deformable backing medium, the spacer spacing a fibrous material that is positioned adjacent to said deformable backing medium apart from the front surface of said deformable backing medium; and
c) optionally, at least one support for supporting a fibrous material in a position adjacent to the front surface of said deformable backing medium.

The invention also provides an apparatus for evaluating the backface signature of a fibrous material, the apparatus comprising:
a) a deformable backing medium compliant with NIJ Standard 0101.06, the deformable backing medium having a front surface; said deformable backing medium being contained in an open face fixture;
b) a spacer defining a space adjacent to said deformable backing medium, the spacer spacing a fibrous material that is positioned adjacent to said deformable backing medium apart from the front surface of said deformable backing medium by at least about ⅛ inch (0.3175 cm), said spacer comprising an element having a border and an interior cavity defined by said border, wherein said deformable backing medium is exposed through said cavity, and wherein said spacer is positioned in direct contact with front surface of the deformable backing medium; and
c) at least one support for supporting a fibrous material in a position adjacent to the front surface of said deformable backing medium.

The invention further provides a method for evaluating the backface signature of a fibrous material, the method comprising:
I) providing an apparatus for evaluating the backface signature of a fibrous material, the apparatus comprising:
  a) a deformable backing medium having a front surface;
  b) a spacer defining a space adjacent to said deformable backing medium, the spacer spacing a fibrous material that is positioned adjacent to said deformable backing medium apart from the front surface of said deformable backing medium; said spacer comprising an element having a border and an interior cavity defined by said border, wherein said deformable backing medium is exposed through said cavity; and
  c) optionally, at least one support for supporting a fibrous material in a position adjacent to the front surface of said deformable backing medium;
II) positioning a fibrous material adjacent to said deformable backing medium, wherein said spacer is positioned between the fibrous material and said deformable backing medium, the fibrous material being spaced apart from the front surface of said deformable backing medium by said spacer;

III) firing at least one projectile at the fibrous material at a target location that corresponds to the interior cavity of said spacer, and such that the projectile impacts the fibrous material at a location that corresponds to the interior cavity of said spacer, and wherein the impact of the projectile on the fibrous material causes a depression in the deformable backing medium; and IV) measuring the depth of the depression in the deformable backing medium.

DETAILED DESCRIPTION OF THE INVENTION

In accordance with the invention, the penetration resistance of a ballistic resistant composite is evaluated by firing projectiles (e.g. bullets) against a ballistic resistant composite according to the conditions of Department of Defense Test Method Standard MIL-STD-662F. The projectiles impact the composite and the backface signature is measured according to the techniques described herein.

Backface signature is the measure of the depth of deflection of body armor due to a bullet impact once the armor stops the projectile from penetrating, indicating the potential blunt trauma experienced by the body underneath the armor. The method for measuring BFS as described herein is a modification of and replacement for the standard method described in NIJ Standard 0101.06. NIJ Standard 0101.06, incorporated by reference herein to the extent consistent herewith, identifies a method of transferring the physical deformation of a composite resulting from a non-penetrating projectile impact into a deformable clay backing where the clay is in direct contact with the back of the armor. The depth of deflection of the clay is then measured to determine BFS. The present method separates the composite from the clay with a suitable spacer so that the bulk of the backface deformation is preferably inside the air gap space. In a real-life helmet or body armor impact situation, backface deformation should result in minimum or no contact with the head or body of the user. In a laboratory testing environment, it is most desired that some minimal amount of depression touch the clay to realize the most accurate measurement of BFS. This is because following a ballistic impact, some degree of retraction of the composite is typical, and thus measuring the fabric deformation only will incorporate some error. The present system eliminates such error. The present system also accomplishes BFS evaluation with minimal clay contact. Minimal clay contact is desired because clay disturbance may affect the accuracy of subsequent BFS measurements as testing is repeated. For example, in current BFS testing which employs flat armor panels in direct contact with the clay backing material surface, the kinetic energy of a high speed projectile is transferred to the armor panel, and that energy is then transmitted as a shockwave throughout the clay block. This shockwave disturbs the clay, typically causing it to partially bulge out of its retaining fixture. This impacts the accuracy of measurements and also requires extra handling of the clay as the bulging clay surface must be scraped off to set the front surface of the clay flush with the open face of the fixture. The present method allows BFS measurement with only minimal clay disturbance. This facilitates accurate repetition of the BFS testing reducing or entirely eliminating measurement error, and achieving improved BFS measurement consistency from shot to shot.

Figure 2:
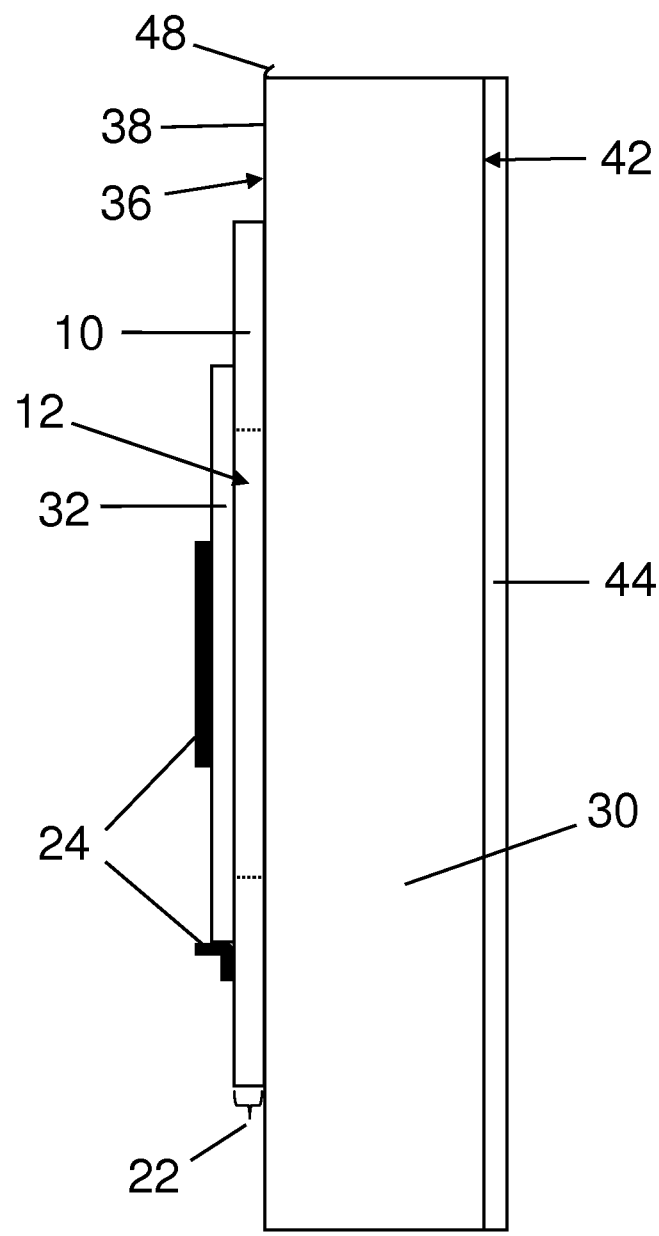
FIG. 2 illustrates a side-view schematic representation of an apparatus incorporating a flat panel spacer with an interior cavity, with a deformable backing medium-containing open face fixture on one side of the spacer and a fibrous material attached to another side of the spacer.
Figure 3:
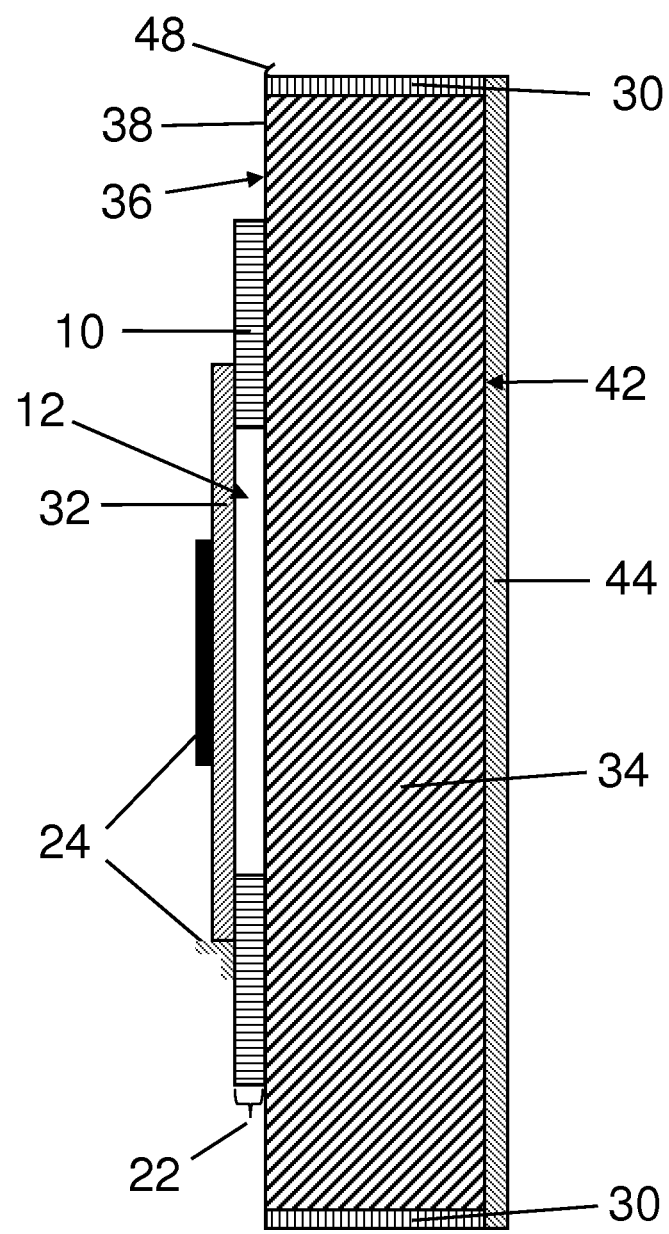
FIG. 3 illustrates a cross-sectional view schematic representation of the apparatus of FIG. 2, illustrating the deformable backing medium within the open face fixture.
Figure 5:
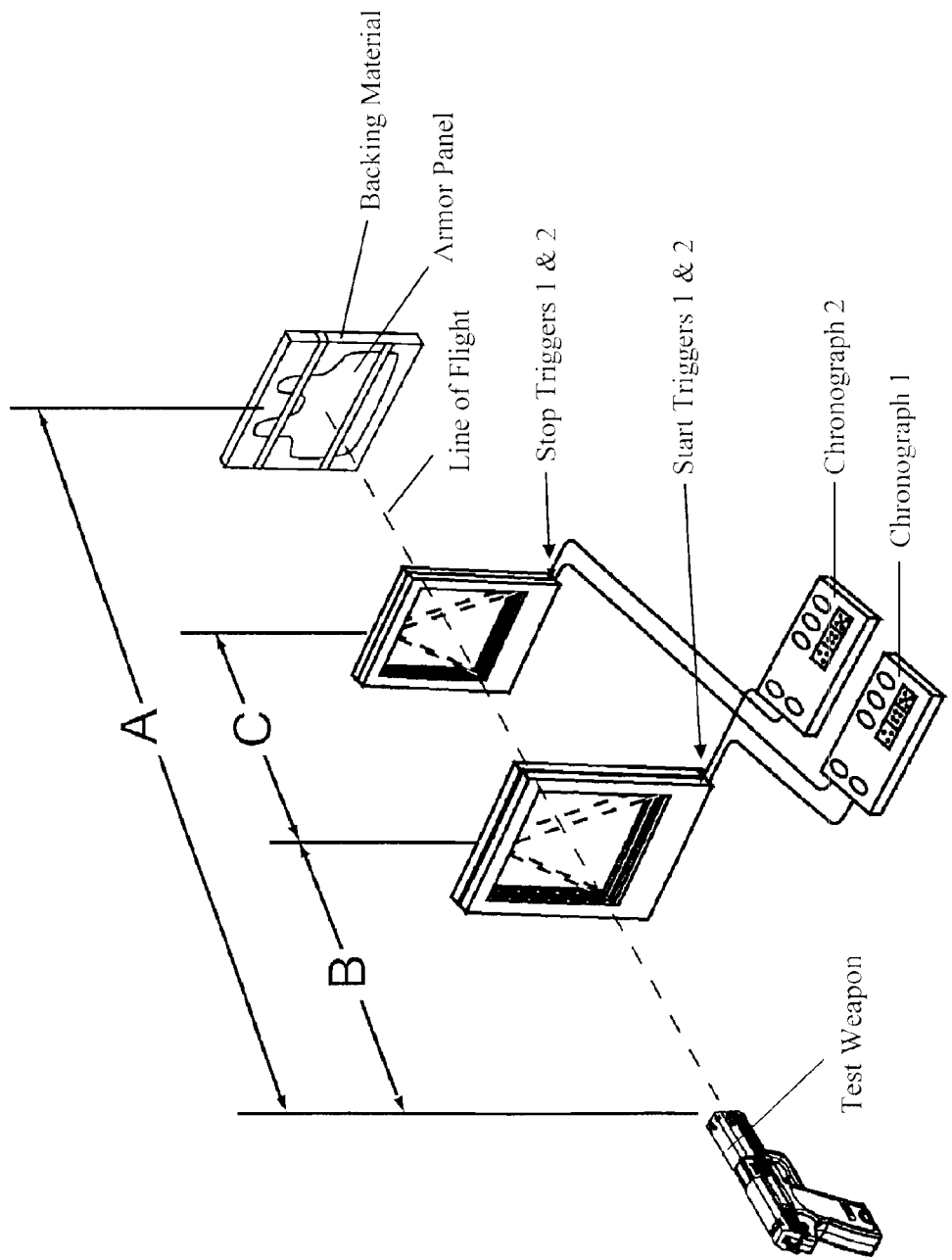
FIG. 5 illustrates a schematic representation of a backface signature testing set-up of the prior art as per NIJ Standard 0101.06 where an armor panel is positioned directly on a deformable backing material.

FIG. 2 illustrates a side-view schematic representation of an apparatus of the invention. FIG. 3 illustrates a cross-sectional view of the same apparatus, showing the deformable backing medium within an open face fixture. As shown, the apparatus of FIGS. 2 and 3 includes a fixture 30 which contains the deformable backing medium 34. Fixture 30 preferably has a hollow, box-like shape fabricated from a rigid metal, such as steel. Fixture 30 is optional herein, but is preferred as a retaining means for the medium 34. When a fixture 30 is not present, the deformable backing medium 34 may be utilized as a free-standing block. When a free-standing block is used, some form of rear support is preferred. For example, a free-standing block of a deformable backing medium 34 may be positioned against a wall or other flat supporting structure. As shown, fixture 30 has a front face 36 and a rear face 42. In accordance with the method of the invention, front face 36 is necessarily open to allow for the exposure of deformable backing medium 34 to permit contact with a fibrous composite sample selected for ballistic testing. It is conventional in the art for backface signature testing to be conducted with a fixture also having a closed rear face, but having an open rear face during ballistic penetration resistance testing, such as $V_{50}$ testing. Accordingly, in the preferred embodiment of the invention, rear face 42 is preferably closed for BFS testing by a removable cover 44 as shown in FIGS. 2 and 3. Removable cover 44 may be fabricated from any suitable material, including, but not limited to, plywood or a suitable metal sheet, such as an aluminum sheet. Thick wood or plywood is conventional as per the specifications of NIJ Standard 0101.06, and is preferred herein. The material used to fabricate cover 44 is not intended to be limiting. Removable cover 44 may optionally be secured to said rear face 42 by one or more reinforcing elements (not shown) such as one or more belts or straps. The use of such reinforcing elements are conventionally known in the art and may likewise be used to secure or assist in securing the fibrous material 32 to spacer 10 as well as secure or assist in securing the spacer 10 to the backing medium 34. Use of such a reinforcing element is preferred to ensure that the distance of the space between the rear surface of the fibrous material 32 and the front surface of the deformable backing medium 34 is equivalent to or approximately equivalent to the depth 22 of the spacer 10. An example of a prior art set-up using reinforcing straps to secure a fibrous material in direct contact with the surface of a deformable backing medium is illustrated in FIG. 5. A similar use of straps is preferred herein as just described.

The deformable backing medium 34 most preferably comprises or consists of a homogenous block of non-hardening, oil-based modeling clay as specified by the BFS testing conditions of NIJ Standard 0101.06. NIJ Standard 0101.06 identifies this clay as Roma Plastilina No. 1 oil-based modeling clay, but any suitable alternative may be used as a substitute. Roma Plastilina No. 1, commercially available from Sculpture House, Inc. of Skillman, N.J., is preferred because it contains wax instead of water and accordingly remains pliable after use and can be reused repeatedly. Equivalent clays commercially available from other manufacturers are also acceptable. According to the NIJ Standard 0101.06 specification, the Roma Plastilina No. 1 clay has a thickness of approximately 5.5 inches (13.97 cm), and this same thickness is preferred for deformable backing medium 34 during BFS testing.

Backing medium 34 has a front surface 38, which is preferably smooth and flat to ensure accurate and consistent measurement of depression depths. Backing medium 34 should also be free of voids. Backing medium 34 is preferably fully contained within fixture 30 such that front surface 38 is planar and fully flush with the front face 36 of fixture 30, i.e. should be even with the reference surface plane defined by the fixtures edges, as similarly required by NIJ 0101.06. Backing medium 34 should also be conditioned and validated as required by NIJ 0101.06.

Figure 1:
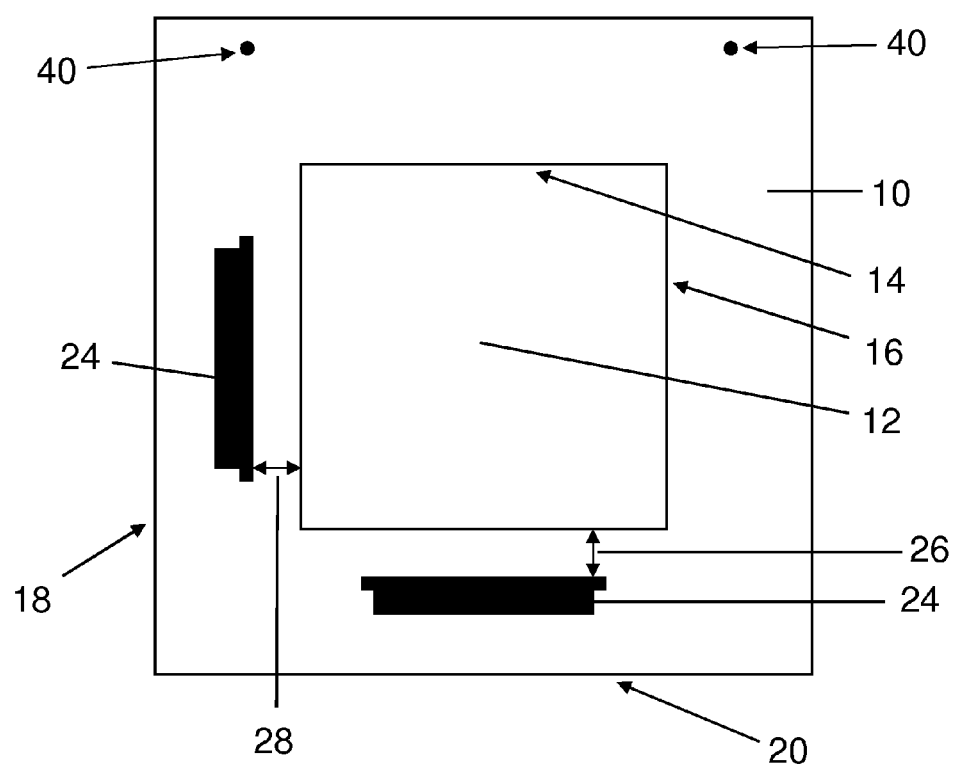
FIG. 1 illustrates a front-view schematic representation of a flat panel spacer having an interior cavity and two bracket supports.

Positioned adjacent to the front surface 38 of deformable backing medium 34 is a spacer 10. Spacer 10 is most preferably in direct contact with the planar front surface 38 of the medium 34. Spacer 10, by virtue of its thickness, defines a space adjacent to said deformable backing medium 34, spacing the front surface 38 of the deformable backing medium 34 apart from a fibrous material 32 such that medium 34 is positioned directly adjacent to spacer 10. As seen in FIG. 1, fibrous material 32 is preferably positioned in direct contact with spacer 10 in order to perform backface signature testing of the fibrous material 32 with the greatest accuracy and repeatability. Fibrous material 32 may be any material or composite for which ballistic penetration or backface signature testing is desired. Neither the composition nor the structure of fibrous material 32 is intended to be limiting herein.

As illustrated in FIG. 1, the spacer 10 preferably comprises an element having an interior cavity 12 through which deformable backing medium 34 is exposed. As described herein, exposure of the deformable backing medium 34 through cavity 12 means that no physical portion of the spacer is 10 is located between fibrous material 32 and backing medium 34 in the area of the cavity 12. This permits the backface deformation of a fibrous material 32 due to a projectile impact to cause an indentation in the backing medium 34 under the proper conditions, i.e. when the backface deformation of the fibrous material 32 is extensive enough to pass through the entire depth of cavity 12, pressing into backing medium 34.

As shown in FIGS. 1-4, a preferred spacer 10 is a flat, preferably rectangular or square panel structure having a flat rear surface that is suitable for being placed flat against the front surface 38 of backing medium 34. Preferred spacer 10 has outer edges 18 and 20 which define a length and width of the spacer 10, respectively. The interior cavity 12 of preferred spacer 10 is defined by interior edges 14 and 16. The dimensions of interior edges 14 and 16 and outer edges 18 and 20 may vary but must permit the apparatus to function as intended, i.e. the spacer 10 must block a fibrous material 32 from directly contacting backing medium 34 prior to a projectile impact, while permitting the deformation of a fibrous material 32 within the area of cavity 12 sufficient to pass through said cavity 12, causing the front surface 38 of the backing medium 34 to be contacted by the fibrous medium 32 only after a projectile impact, and thereby causing a measurable indentation in or measurable deformation of the backing medium 34 as a result of said contact.

Of significant importance is the depth 22 of the spacer 10, which is equivalent to the depth the cavity 12. As with edges 14, 16, 18 and 20, the depth 22 of spacer 10 may vary, but in the most preferred embodiments of the invention, the depth of spacer 10 is preferably equal to or less than ½" (12.7 mm) in order to provide an appropriate approximation of the typical spacing between a helmet shell and a human head in an actual helmet article which includes conventional padding or a conventional suspension/restraint system. Preferably, the depth 22 of spacer 10 is from about 1/12" (~2.127 mm) to about 1" (25.4 mm), more preferably from about ⅛" (3.175 mm) to about ½" (12.7 mm), even more preferably from about ¼" to about ½" (12.7 mm). Most preferably, the depth of spacer 10 is ½" (12.7 mm). As stated above, the spacer 10 defines the space adjacent to the deformable backing medium 34, spacing the fibrous material 32 apart from front surface of the backing medium 34. Accordingly, when a fibrous material 32 is positioned adjacent to and in direct contact with the spacer 10 as shown in FIGS. 2 and 3, the distance of the space between the rear surface of the fibrous material 32 and the front surface of the deformable backing medium 34 is equivalent to or approximately equivalent to the depth 22 of spacer 10.

Figure 4:
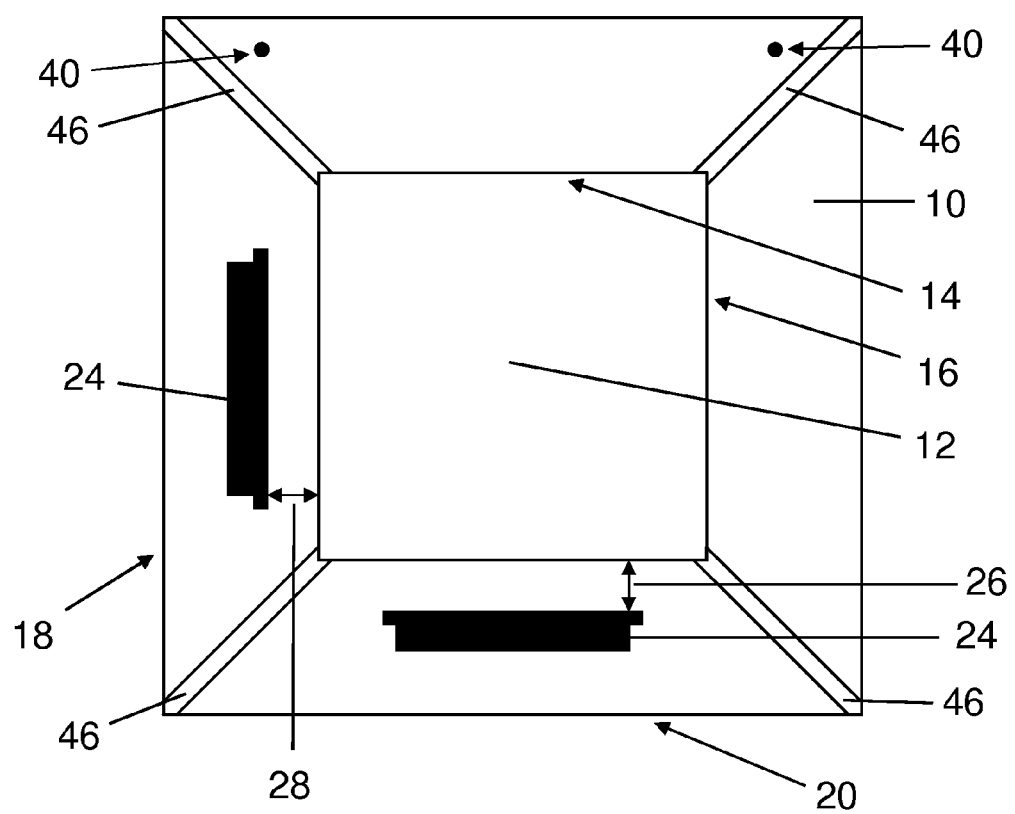
FIG. 4 illustrates a front-view schematic representation of a flat panel spacer having an interior cavity and two bracket supports, and further having air vent channels at each corner of the spacer.

Spacer 10 may be fabricated from any suitable material. Preferably, spacer 10 is fabricated from wood, plastic, or a rigid metallic material, such as multipurpose aluminum stock. Rigid multipurpose aluminum is preferred because it is relatively inexpensive, relatively lightweight, and relatively simple to cut and form into any desirable shape. Spacer 10 may be fabricated into any useful regular or irregular shape, but a rectangular or square shape with a similarly shaped cavity is preferred, as illustrated in FIGS. 1 and 4.

In order to support a fibrous material 32 in a position adjacent to the front surface of the deformable backing medium 34 and in direct contact with the spacer 10 as shown in FIGS. 2 and 3, it is preferred that the fibrous material 32 be supported and/or held in place by at least one support 24, such as one or more brackets. FIGS. 1 and 4 illustrate a preferred embodiment including two bracket supports 24, one being positioned to support the bottom of a fibrous material 32 and another being positioned to support a side of fibrous material 32, which is most useful when the fibrous material 32 is fabricated in a conventional square or rectangular shape. As seen in FIGS. 1 and 4, reference numeral 26 represents the distance from a bottom supporting bracket to an edge 14 of cavity 12. Reference numeral 28 represents the distance from a side supporting bracket to an edge 16 of cavity 12. These distances are not intended to be limiting. When incorporated, the one or more supports 24 may be fabricated as integral elements of the spacer 10 or may be elements that are separately attached to the spacer 10. Most preferably they are attached to the spacer rather than integral elements.

As previously stated, spacer 10 may be secured to the front surface 38 of backing medium 34 using a reinforcing element, such as a belt or a strap. In an alternate preferred embodiment, spacer 10 may be held or hung in such a position adjacent to backing medium 34 via a hanging device (not shown), such as a wire, a string or a rope, preferably a wire. In this embodiment, a hanging device may be attached to the spacer 10 via mounting elements 40. Mounting elements 40 may be screws or any suitable substitute. The type of mounting element is not intended to be limiting. The hanging device is preferably connected to or hooked onto the fixture 30 via a hook 48, thereby mounting the spacer 10 on the fixture 30. In a preferred embodiment of the invention, the spacer 10 is both hung on the fixture 30 and secured to the backing medium 34 with a reinforcing element like a belt or strap.

In addition, while it is desired to hold the fibrous material 32 tightly against the spacer 10, it has been found that such may potentially cause air to be entrapped between the panel of fibrous material 32 and the surface of spacer 10. This is problematic because it is preferred for a single fibrous material 32 to be used multiple times to accumulate multiple data points, but entrapped air having no appropriate venting route may damage the fibrous material 32 when a projectile impacts the material 32, or may affect the shape/depth of the backface deformation of the fibrous material 32. This may affect the reliability of results and/or prevent reuse of the fibrous material 32. As shown in FIG. 4, this problem may be addressed by fabricating spacer 10 to include one or more air venting channels 46 recessed within the border of the spacer 10. The one or more air venting channels 46 are located at an interface of the spacer 10 with an adjacent fibrous material 32 and preferably extend from an edge or corner of the interior cavity 12 through at least one of the corners or outer edges 18 and/or 20 of the spacer 10 border. Most preferably, the spacer 10 comprises a plurality of air venting channels 46, each channel 46 extending both through an exterior edge or corner of said spacer 10 border and through an interior edge or corner of said spacer 10 border, wherein said interior edge of said spacer 10 defines the cavity 12 of the spacer 10.

A conventional set-up of the prior art for backface signature testing is illustrated in FIG. 5. A projectile is fired from a testing weapon which is positioned at a distance A from a backing material fixture. Located in between the testing weapon and the backing material fixture are Start and Stop Triggers 1 and 2, which are employed to measure the velocity of the projectile fired at an armor test panel. As shown by the Line of Flight in FIG. 5, a fired projectile will first pass through Start Triggers 1 & 2, which transmits a signal to Chronograph 1, and then through Stop Triggers 1 & 2, which transmits a signal to Chronograph 2. Data from these signals are used to calculate projectile velocity. Distances A, B and C as shown in FIG. 5 are regulated by NIJ Standard 0101.06 for various types of armor. For Type I, II, II-A and III-A armors, A is 5 m, and for Type III and IV armors, A is 1.5 m. For Type I, II, II-A and III-A armors, B must be a minimum of 2 m, and for Type III and IV armors, B must be a minimum of 1.2 m. For all armor types, C is approximately 1.5 m. These identified distances are standardized NIJ requirements and are presented herein only for purposes of illustration. The backface signature testing set-up for the present invention is preferably the same as this conventional prior art set-up except for the presence of spacer 10 between fibrous material 32 and backing material 34. The prior art set-up of FIG. 5 requires the placement of the armor test panel in direct contact with the backing material.

According to the preferred testing protocol of the present invention, the backing medium 34 is retained in a fixture 30 rather than utilizing the backing medium 34 as a free-standing block of clay without a fixture. The fixture 30 may be supported by and secured to a stand that elevates the assembly to a desired height, as would be understood by one skilled in the art. The spacer 10 is mounted on the fixture 30 via a wire which is attached to the spacer 10 via mounting screws 40. A fibrous material 32 may be positioned on the spacer 10 either prior to or after mounting the spacer 10 on the fixture 30, where fibrous material 32 is positioned adjacent to the deformable backing medium 34 such that the spacer 10 is positioned between the fibrous material 32 and the deformable backing medium 34 as described herein. The fibrous material 32 and spacer 10 are then most preferably secured to the fixture 30 using two adjustable straps analogous to the reinforcing straps shown in FIG. 5. The adjustable straps may be positioned in contact with the front of the fibrous material 32 in any position that is not within the area of the fibrous material 32 which is located in front of cavity 12.

Once all elements of the system are in place, the tester may proceed with firing at least one projectile at the fibrous material 12 at a target location that corresponds to the interior cavity 12 of said spacer 10 such that the projectile impacts the fibrous material 32 at a location that corresponds to the interior cavity 12 of said spacer 10. Any impact of the projectile that causes a deformation of the fibrous material 32 which is sufficient to extend through the depth 22 of the cavity 12 and into contact with the front surface 38 of the deformable medium 34 will cause a measurable depression or indentation in the deformable backing medium 34. The depth of this depression in the backing medium 34 is then measured using well known techniques, and the depression depth represents the backface signature of the material. These steps of firing a projectile and measuring the BFS may be repeated at least once using a similar projectile and at an equal or similar firing velocity, and an average depth of depression may be calculated if there are any differences in measured BFS depth from shot to shot.

Depending on conditions such as the type of fibrous material 32 being tested, the projectile type and the projectile velocity, it is possible that the deformation of the fibrous material 32 may not be extensive enough to extend through the entire depth 22 of the spacer 10, thereby failing to indent the deformable backing material 34. In such circumstances, testing should be repeated utilizing a spacer 10 having a reduced depth 22, because in general, some clay contact is necessary to accurately measure BFS. Accordingly, lower energy threats and/or fibrous composites of greater areal density will necessitate the use of spacers 10 having smaller depths 22 to ensure the minimal clay contact.

It should be understood that there are various foreseeable alternatives to the preferred apparatus assembly as described herein. For example, rather than utilizing a frame-like flat panel spacer 10 having an interior cavity 12, the desired spacing between a fibrous material 32 and backing material 34 may be achieved, for example, by recessing backing material 34 within fixture 30 by the desired distance, such that the front surface 38 of backing material 34 is not fully flush with the front face 36 of fixture 30. In this embodiment, the portion of fixture 30 between fibrous material 32 and backing material 34 would then constitute the spacer 10. Front surface 38 of backing material 34 should remain flat and planar. In this embodiment, fibrous material 32 may be positioned in contact with the front face of fixture 36, but would not be in contact with front surface 38 of backing material 34. In another foreseeable embodiment, the assembly may be set up, for example, wherein the backing material 34, either retained within a fixture 30 or not, is laid on the ground or on some other flat surface, with a spacer 10 then being laid on top of the backing material 34 or fixture 30, and the fibrous material 32 then being laid on top of the spacer 10, utilizing gravity to maintain each element in its proper position, with or without reinforcing elements/straps. For example, a free-standing block of medium 34 may be laid on the ground such that the front surface 38 is facing upward, and with a firing assembly set up to fire from above the deformable medium 34. In yet another foreseeable embodiment, fibrous material 32 may be secured in a position adjacent to yet spaced from a deformable backing medium 32 using tubes (inflatable or not inflatable), rods, strips fabricated from metal, wood, plastic or any other suitable material, or any other spacing means suitable to achieve the purposes described herein, wherein said tubes, rods, strips or other spacing means may include a plurality of spacing means that are either connected to each other or disconnected from each other. Accordingly, the apparatus of the invention is intended to encompass any assembly which includes at minimum a) a deformable backing medium having a front surface; and b) at least one spacer defining a space adjacent to said deformable backing medium, the at least one spacer spacing a fibrous material that is positioned adjacent to said deformable backing medium apart from the front surface of said deformable backing medium.

The following examples serve to illustrate the invention.

EXAMPLES

The standard method for measuring BFS of soft armor is outlined by NIJ Standard 0101.04, Type IIIA, where an armor sample is place in contact with the surface of a deformable clay backing material. The backface signature of four different materials was tested for molded panels having three different composite areal densities. Each panel was tested both according to the standardized method of NIJ Standard 0101.06 where the panels to be tested were placed in direct contact with the front surface of a deformable clay (identified as "Panel Directly on Clay—No Air Gap"), as well as according to the method of the invention utilizing a custom machined, frame-type flat panel spacer between the composite article and the clay block as illustrated in FIGS. 1-4 having an interior cavity with a ½ inch (12.7 mm) cavity depth (identified as "Panel Spaced From Clay—½" Air Gap").

The spacer used was fabricated from ½" multipurpose aluminum stock having dimensions of 18"×18"×½" (L×W×D). The interior cavity had dimensions of 10"×10"×½" (L×W×D). One inch wide aluminum brackets were attached to the spacer as shown in FIG. 1, the brackets being positioned perpendicular to each other. Each bracket was positioned approximately 1" from the interior cavity. The spacer was mounted on a fixture using a wire, which wire was attached to the spacer with two ½" mounting screws. Each molded panel that was tested measured approximately 12"×12" (L×W) with the depth varying as determined by the selected composite areal densities shown in Tables 1 and 2. The fixture was filled with a 5.5" thick square block of Roma Plastilina No. 1 oil-based modeling clay having dimensions of approximately 24"×24"×5" (L×W×D), and the block was flush with the front face of the fixture. The fixture was a rigid, hollow box-shaped structure fabricated from steel, having an open front face and open rear face, and having dimensions of approximately 24"×24"×5" (L×W×D). No rear cover was used, but a ¾" thick sheet of plywood (approximate dimensions: 24"×24"×¾" (L×W×D)) as a rear cover was available. A separate spacer having air venting channels in each corner (approximate dimensions: ³⁄₁₆"×¼" (D×W)) as shown in FIG. 4 was also available but not used. All testing was conducted at a room temperature of approximately 72° F. Projectiles were fired at the composite articles at target locations corresponding to the interior cavity of the spacer. The projectiles impacted the composite article at locations corresponding to the interior cavity of the spacer, and except for Example 12, each projectile impact caused a measurable depression in the clay. In Example 12, the full depth of panel deformation failed to extend beyond the depth of the spacer and thus is less than ½". All of the BFS measurements in Table 1 refer only to the depth of the depression in the clay as per the inventive method and do not take into account the depth of the spacer element, i.e. the BFS measurements in Table 1 do not include the actual distance between the composite and the clay.

Examples 1-12

TABLE 1

| | Panel spaced from Clay - ½" Air Gap | | | |
|---|---|---|---|---|
| EXAMPLE | PRODUCT | 1.26 psf A.D. | 1.58 psf A.D. | 2.21 psf A.D. |
| 1-3 | A | 18.75 | 14.125 | 8.25 |
| 4-6 | B | 24.75 | 20.5 | 14.125 |
| 7-9 | C | 15.75 | 9.875 | 3.125 |
| 10-12 | D | 3.75 | 1.75 | 0 |

Examples 13-24 (Comparative)

TABLE 2

| | Panel Directly on Clay - No Air Gap | | | |
|---|---|---|---|---|
| EXAMPLE | PRODUCT | 1.26 psf A.D. | 1.58 psf A.D. | 2.21 psf A.D. |
| 13-15 | A | 23.375 | 22 | 23 |
| 16-18 | B | 24.5 | 24.625 | 24.125 |
| 19-21 | C | 20.875 | 21.625 | 22.375 |
| 22-24 | D | 21.25 | 21.5 | 19.25 |

Each of the four products tested were different and are identified generically as products A, B, C and D. The specific composition and structure of each tested product was kept constant for all testing except for changes in composite areal density ("A.D.", measured in lb/ft² (psf)) as designated in Tables 1 and 2. Other than changes in the A.D., the specific composition and structure of each tested product as kept constant is irrelevant. The data in Table 1 does not include the depth of the space between the composites and the clay, but should be added to identify the full extent of the composite deformation. As shown by a comparison of the data in Table 1 and Table 2, data acquired using the testing protocol of the present invention helps to clearly identify differences in the backface signature for composites of varying areal densities, while data obtained using the conventional method of the prior art is unreliable and inconclusive. This difference is significant when it is desired to evaluate backface signature with accuracy, repeatability and improved correlation to the expected backface signature of shaped ballistic resistant composites in actual field use.

Examples 25-40

Delamination Measurement

The backface signature of four additional products, identified generically as products I, II, III and IV. The different products were subjected to various fiber treatments, or were left untreated. Each was tested for backface signature using the ½" air gap method of the invention. For comparison, backface deformation was also measured by disregarding the depression in the clay and measuring the deformation of the composite itself. Such is referred to as "delamination"

because it is not the clay depression which is being measured. Accordingly, delamination in Table 3 refers to the measurement of the depth of rear deformation of the actual tested panels, rather than the depth of depression in the backing material. This measurement of delamination will be less than the BFS measurement plus the ½" (12.7 mm) air gap depth because after a projectile impact, the fabric at the area of impact partially retracts. The delamination measurement is taken after said retraction, while the BFS measurement with the air gap method described herein records the full extent of rear deformation of the fabric. Deformation after said retraction is typically measured by cutting a cross-section of the panel and measuring the depth from the plane of the undamaged rear surface of the panel to the deepest outer portion of the deformed area.

For each example, BFS was measured for 12"×12" square samples having an areal density of 2.0 lb/ft$^2$ (psf) and a fiber areal density (areal density of a single ply of parallel fibers, i.e. one unitape) of 53 grams/m$^2$ (gsm). For each example, BFS was measured against a 9 mm, 124-grain FMJ RN projectile fired at a velocity of about 1430 feet/second (fps)±30 fps.

TABLE 3

| Example | Product | BFS @ 2.0 psf | | Delamination @ 2.0 psf | | BFS plus ½" gap minus Delam @ RT (mm) | BFS plus ½" gap minus Delam @ 160° F. (mm) |
| --- | --- | --- | --- | --- | --- | --- | --- |
| | | RT (mm) | 160° F. (71.11° C.) (mm) | RT (mm) | 160° F. (71.11° C.) (mm) | | |
| 25 | I | 9.4 | 13.1 | 17.3 | 14.7 | 4.8 | 11.1 |
| 26 | I | 6.5 | 9.8 | 13.1 | 12.3 | 6.1 | 10.2 |
| 27 | I | 3.38 | 6.25 | 11 | 11.5 | 5.08 | 7.45 |
| 28 | II | 8.3 | 11.3 | 16.3 | 17.0 | 4.7 | 7 |
| 29 | II | 10.5 | 11.5 | 14.5 | 18.4 | 8.7 | 5.8 |
| 30 | II | 5.3 | 7.5 | 13.3 | 14.1 | 4.7 | 6.1 |
| 31 | II | 1.88 | 4.69 | 12.25 | 11.94 | 2.33 | 5.45 |
| 32 | II | 2.25 | 4.13 | 12.13 | 15.5 | 2.82 | 1.33 |
| 33 | III | 12.4 | 14.85 | 15.6 | 14.85 | 9.5 | 12.7 |
| 34 | III | 11.5 | 10.3 | 11.8 | 14.3 | 12.4 | 8.7 |
| 35 | III | 6.9 | 11.7 | 9.8 | 10.1 | 9.8 | 14.3 |
| 36 | III | 5.13 | 6.13 | 12.75 | 12.13 | 5.08 | 6.7 |
| 37 | IV | 5.3 | 14.3 | 12.5 | 14.8 | 5.5 | 12.2 |
| 38 | IV | 6.25 | 9.625 | 14.25 | 13.75 | 4.7 | 8.575 |
| 39 | V | 3.75 | 6.06 | 14.88 | 13.7 | 1.57 | 5.06 |
| 40 | VI | 3.13 | 6.38 | 12.75 | 13.56 | 3.08 | 5.52 |

The last two columns in Table 3 identifying BFS plus ½" (12.7 mm) gap minus delamination identify the amount of fabric retraction and illustrate the greater accuracy of the air gap spacer BFS measurement method for measuring the full expected extent of BFS of hard armor in actual field use.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. An apparatus for evaluating the backface signature of a fibrous material, the apparatus comprising:
   a) a deformable backing medium having a front surface, wherein said deformable backing medium comprises clay;
   b) a spacer defining a space adjacent to said deformable backing medium, the spacer spacing said fibrous material that is positioned adjacent to said deformable backing medium apart from the front surface of said deformable backing medium; wherein said spacer comprises a flat, rigid panel having a border and an interior cavity defined by said border, wherein said deformable backing medium is exposed through said cavity, and wherein the spacer is in direct contact with the front surface of the deformable backing medium.

2. The apparatus of claim 1 wherein said deformable backing medium is contained in an open face fixture, and wherein the fibrous material is present and the spacer is positioned between the fibrous material and the deformable backing medium whereby the fibrous material and the deformable backing medium are separated by at least about ⅛ inch.

3. The apparatus of claim 1 wherein said spacer has a thickness of at least about ⅛ inch (0.3175 cm) and said interior cavity has a depth that is equal to the thickness of said flat panel.

4. The apparatus of claim 1 wherein said space is at least about ½ inch (1.27 cm).

5. The apparatus of claim 1 wherein said deformable backing medium is contained in an open face box-shape fixture, wherein said spacer comprises a flat panel having an interior cavity having a depth of at least about ½ inch (1.27 cm), wherein said deformable backing medium is exposed through said cavity, and wherein said spacer is positioned in direct contact with front surface of the deformable backing medium.

6. The apparatus of claim 1 wherein said deformable backing medium is contained in a fixture having both an open front face and an open rear face, wherein said open rear face of the fixture is at least partially covered by a removable cover, wherein said removable cover is optionally secured to said rear face by a reinforcing element.

7. The apparatus of claim 1 wherein said optional at least one support is provided and comprises at least one supporting bracket that is attached to or integral with said spacer.

8. The apparatus of claim 1 wherein the fibrous material is positioned adjacent to said deformable backing medium, wherein said spacer is positioned between the fibrous material and said deformable backing medium, and said fibrous material is spaced apart from the front surface of said deformable backing medium by said spacer, and wherein said deformable backing medium consists essentially of clay.

9. The apparatus of claim 8 wherein said fibrous material is secured to said spacer by at least one reinforcing element, said at least one reinforcing element also optionally securing said spacer to said deformable backing medium.

10. The apparatus of claim 1 wherein said at least one support and said spacer comprise a single element that both supports said fibrous material in a position adjacent to the front surface of said deformable backing medium and also spaces said fibrous material that is positioned adjacent to said deformable backing medium apart from the front surface of said deformable backing medium.

11. The apparatus of claim 1 wherein said spacer further comprises at least one air venting channel recessed within said border, said at least one channel extending through at least one edge of said border and being provided at an interface of said spacer and adjacent to said fibrous material.

12. The apparatus of claim 11 wherein said spacer comprises a plurality of air venting channels, each channel extending through both an exterior edge of said border and through an interior edge of said border, wherein said interior edge of said border defines said cavity of said spacer.

13. An apparatus for evaluating the backface signature of a fibrous material, the apparatus comprising:
   a) a deformable backing medium compliant with NIJ Standard 0101.06, the deformable backing medium comprising clay and having a front surface; said deformable backing medium being contained in an open face fixture;
   b) a spacer defining a space adjacent to said deformable backing medium, the spacer spacing said fibrous material that is positioned adjacent to said deformable backing medium apart from the front surface of said deformable backing medium by at least about ⅛ inch (0.3175 cm), said spacer comprising a flat, rigid panel having a border and an interior cavity defined by said border, wherein said deformable backing medium is exposed through said cavity, and wherein said spacer is positioned in direct contact with front surface of the deformable backing medium; and wherein the spacer is in direct contact with the front surface of the deformable backing medium; and
   c) at least one support for supporting said fibrous material in a position adjacent to the front surface of said deformable backing medium.

14. The apparatus of claim 13 which further comprises said fibrous material positioned adjacent to said deformable backing medium, which fibrous material is supported in a position adjacent to the front surface of said deformable backing medium by at least one support, which fibrous material is spaced apart from the front surface of said deformable backing medium by said spacer, and wherein said deformable backing medium consists of clay.

15. The apparatus of claim 13 wherein said spacer further comprises at least one air venting channel recessed within said border, said at least one channel extending through at least one edge of said border and being provided at an interface of said spacer and adjacent to said fibrous material.

16. A method for evaluating the backface signature of a fibrous material, the method comprising:
   I) providing an apparatus for evaluating the backface signature of said fibrous material, the apparatus comprising:
   a) a deformable backing medium having a front surface, wherein said deformable backing medium comprises clay;
   b) a spacer defining a space adjacent to said deformable backing medium, the spacer spacing said fibrous material that is positioned adjacent to said deformable backing medium apart from the front surface of said deformable backing medium; said spacer comprising a flat, rigid panel having a border and an interior cavity defined by said border, wherein said deformable backing medium is exposed through said cavity;
   II) positioning said fibrous material adjacent to said deformable backing medium, wherein said spacer is positioned between the fibrous material and said deformable backing medium, the fibrous material being spaced apart from the front surface of said deformable backing medium by said spacer;
   III) firing at least one projectile at the fibrous material at a target location that corresponds to the interior cavity of said spacer, and such that the projectile impacts the fibrous material at a location that corresponds to the interior cavity of said spacer, and wherein the impact of the projectile on the fibrous material causes a depression in the deformable backing medium; and
   IV) measuring the depth of the depression in the deformable backing medium.

17. The method of claim 16 wherein steps III) and IV) are repeated at least once using another projectile and at an equal or similar firing velocity, and calculating an average depth of depression in the deformable backing medium.

18. The method of claim 16 wherein the projectiles are fired at the fibrous material according to the conditions of Department of Defense Test Method Standard MIL-STD-662F.

19. The apparatus of claim 1, further comprising at least one support for supporting said fibrous material in a position adjacent to the front surface of said deformable backing medium.

20. The method of claim 16, wherein the apparatus further comprises at least one support for supporting said fibrous material in a position adjacent to the front surface of said deformable backing medium.

* * * * *